United States Patent [19]
Vidra

[11] 4,205,061
[45] May 27, 1980

[54] ORAL ANTIMICROBIAL COMPOSITIONS

[75] Inventor: James D. Vidra, Clinton, N.J.

[73] Assignee: Johnson & Johnson, New Brunswick, N.J.

[21] Appl. No.: 924,764

[22] Filed: Jul. 14, 1978

[51] Int. Cl.² .................. A61K 7/24; A61K 31/44; A61K 31/60; A61K 31/625

[52] U.S. Cl. .................. 424/55; 424/230; 424/232; 424/263

[58] Field of Search .................. 424/55, 230, 232, 263

[56] References Cited
U.S. PATENT DOCUMENTS

| | | | |
|---|---|---|---|
| 3,852,436 | 12/1974 | Harich | 424/232 |
| 3,992,519 | 11/1976 | Hofmann et al. | 424/55 |
| 4,022,880 | 5/1977 | Vinson et al. | 424/55 |

FOREIGN PATENT DOCUMENTS 137233  7/1961  U.S.S.R. .................. 424/55

OTHER PUBLICATIONS

McCutcheon's Detergents & Emulsifiers, 1971 Annual p. 1.

*Primary Examiner*—Douglas W. Robinson
*Attorney, Agent, or Firm*—Steven P. Berman

[57] ABSTRACT

Novel oral antimicrobial compositions comprising a synergistic combination of a specific halogenated salicylanilide and a specific quaternary ammonium compound are disclosed.

5 Claims, No Drawings

ORAL ANTIMICROBIAL COMPOSITIONS

BACKGROUND OF THE INVENTION

This invention relates to "oral compositions" which term is used herein to designate products which, in the ordinary course of usage, are retained in the oral cavity for a time sufficient to contact substantially all of the dental surfaces but are not intentionally ingested. Such products include, for example, dentifrices, mouthwashes, chewing gums, prophylaxis pastes, non-abrasive gels, topical solutions and the like. This invention more specifically relates to oral compositions which exhibit antimicrobial properties which help to retard the accumulation of dental plaque and/or calculus on the teeth and gums.

Dental plaque is a complex organic film which adheres to and coats the oral hard and soft tissues. The formation and properties of dental plaque are extremely important in the maintenance of oral health since plaque harbors the bacteria which produce dental caries, gingivitis and periodontitis. In fact, dental plaque is composed essentially of bacterial colonies growing in an interbacterial organic matrix that provides adherence of the colonies to the teeth and gingiva and coherence of the colonies to one another. Thus, the elimination or inhibition of dental plaque is related to and beneficial in reducing the incidence of dental caries, gingival inflammation and periodontitis.

As is well known to those skilled in the art, dental caries is caused principally by dissolution of tooth mineral by biologically produced intra-oral acids. Such biologically produced intra-oral acids primarily are produced by some of the bacterial colonies that constitute dental plaque. Gingival inflammation, which is the first stage of the more severe periodontitis, is produced by the inflammatory products of bacterial plaque metabolism. Among these bacterial metabolites one can mention hydrolytic enzymes, endotoxins and antigens. Thus, the elimination of the medium which comprises such caries and gingivitis producing bacteria is believed to directly affect the incidence of dental caries and periodontitis.

The formation of dental plaque is not fully understood but it is known to result from the growth and colonization of various strains of oral bacteria on the surface of the teeth and gingiva. Further, there is believed to be a direct relationship between the ability of dental plaque to induce the precipitation (crystallization) of calcium salts on the surface of the teeth and formation of dental calculus.

Dental calculus is a hard deposit found on the surfaces of the teeth which results from the precipitation of calcium salts in an organic matrix, primarily plaque. Thus, calculus can be defined as calcified plaque. Calculus is related to dental health since its presence is associated with pathological changes in the bone, gingiva and other supporting periodontal structures. Thus, the elimination and retardation of the formation of dental plaque is an important factor in dental hygienic and health programs not only in the reduction of dental caries and periodontal disease but also the reduction of the formation of dental calculus.

The utilization of antibacterial or antimicrobial agents such as antiseptics and germicides for topical application in the oral cavity is well known in the art. By way of explanation, an antiseptic ordinarily is considered to be an agent which stops or inhibits the growth of microorganisms without necessarily killing them. In contrast, a bacteriocide or germicide is any substance which kills or destroys bacteria. Frequently, the difference between bacteriostatic and bacteriocidal effects is a quantitive function of the concentration of the antibacterial agents or a qualitative function of the agent itself.

Less irritating antiseptics find wide usage for topical application on the oral mucosa for the control of minor infections and on dried mucosa in preparation for needle insertion. Antiseptics too irritating for use on soft tissue find application within the tooth structure for root canal sterilization or cavity medication. Germicides have also been incorporated in commercial mouthwashes which are medicated liquids used for cleaning the mouth or treating disease states in the oral mucous membrane.

The use of such antiseptic agents has many times resulted in severe staining problems with the teeth which would mitigate against their use even if they were effective against plaque.

SUMMARY OF THE INVENTION

It is an object of this invention to provide improved oral compositions.

It is another object of this invention to provide improved oral compositions which exhibits antimicrobial properties to aid in the prevention of plaque and gingival diseases.

It is a further object of this invention to provide improved antimicrobial oral compositions which do not present significant tooth staining problems.

Other objects of this invention will be set forth in, or be apparent from, the following detailed description of the invention.

The foregoing objects and other features and advantages of the present invention are achieved by oral compositions comprising a synergistic combination of antimicrobial agents which effectively reduce the formation of plaque without adversely staining the teeth. More specifically, the present invention relates to oral composition comprising a synergistic combination of a specific halogenated salicylanilide and a specific quaternary ammonium compound.

DETAILED DESCRIPTION OF THE INVENTION

In general, this invention comprises a synergistic combination of a specific halogenated salicylanilide and a specific quaternary ammonium compound. The term "synergistic combination" as used herein refers to a mixture of two discrete compounds which display a degree of total antimicrobial activity which is greater than the average of the sum of antimicrobial activity of the compounds taken individually.

The specific halogenated salicylanilide which has been found useful in the present invention is 3,5-dibromo-3'-trifluoromethylsalicylanilide which is of the formula

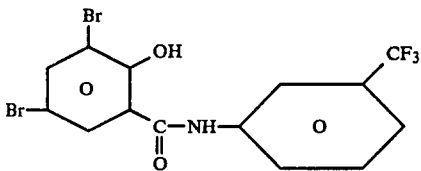

Surprisingly 3,5-dibromo-3'-trifluoromethylsalicylanilide does not exhibit the toxicity or photosensitivity problems which have been observed with other halogenated salicylanilides and would therefore be satisfactory for oral hygiene uses.

The other antimicrobial compound in the synergistic combination is a specific quaternary ammonium compound, cetylpyridinium chloride, which is of the formual

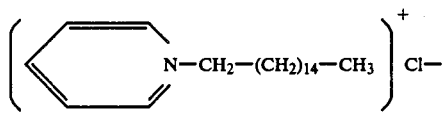

The ratio of the compounds in the synergistic combinations of this invention can vary from about 10:1 to 1:10, preferably a ratio of about 1:1.

The foregoing synergistic combination of 3,5-dibromo-3'-trifluoromethylsalicylanilide and cetylpyridinium chloride is preferably applied to the oral hard and soft tissues by means of a carrier suitable for use in the oral cavity. Suitable carriers include dentifrices, prophylaxis, pastes, mouthwashes, nonabrasive gels, chewing gums, topical solutions, and the like. When used in such compositions, the synergistic antimicrobial compositions are present in about 0.05% to about 0.20% by weight of the total compositions. In the case of topical solutions and mouthwashes, suitable carriers include water and other liquids. Other carriers include various compatible plastics, e.g., nylon, polyethylene, polypropylene and the like, and other materials, e.g., natural bristles, wood, and the like, which may be formed into toothbrushes or interdental stimulators and thus utilized to apply the active agents of the present invention to the oral hard and soft tissues. Also, other carriers include waxes, plastics, or any other binders or sizings used on dental flosses and tapes or chewing gum which contact the oral hard and soft tissues during use or consumption. Indeed, substantially any device or implement capable of supplying the active agents to the oral hard and soft tissues may serve as a suitable carrier in accordance with this invention.

DENTIFRICE PREPARATIONS

Compositions adapted for regular home use such as dentifrice preparations and the like typically comprise about 20–95% by weight of a compatible cleaning and polishing agent as a carrier suitable for use in the oral cavity. The synergistic antimicrobial combinations of the present invention should comprise from about 0.05% to 0.2% by weight of the dentifrice preparation.

Various compatible cleaning and polishing agents suitable for use in the dentifrice embodiments of this invention are known in the art including insoluble sodium metaphosphate, calcium pyrophosphate, calcium hydrogen phosphate dihydrate, anhydrous calcium hydrogen phosphate, and substantially water impervious crosslinked thermo-setting, highly polymerized synthetic resins, e.g., melamine formaldehyde resins, as described in U.S. Pat. No. 3,070,510. Preferably, zirconium silicate or mixtures of zirconium silicate with other cleaning and polishing agents, e.g., talc, as set forth and described in U.S. Pat. No. 3,450,813 may be used as the cleaning and polishing agent. Also, mixtures of such polishing agents may also be employed. The dentifrice preparations may be prepared in a conventional manner and will usually include additional ingredients to render the overall composition commercially acceptable to consumers.

Dentifrices require a binder substance to impart desired textural properties. Natural gum binders such as gum tragacanth, gum karaya and gum arabic and seaweed derivatives such as Irish moss and alginates, and water soluble cellulose derivatives, such as hydroxyethyl cellulose and sodium carboxymethyl cellulose, can be used for this purpose. Desirably, those materials are employed which are most compatible with the antimicrobial agents. Binders which have no ionic groups, such as hydroxyethyl cellulose, are especially preferred; however, selected ionic binders can occasionally be used. Improvements in texture can also be attained by including an additional material such as colloidal magnesium aluminum silicate. Thickening agents in an amount of from 0.5 to 5.0% by weight can also be used to form a satisfactory dentifrice.

Dentifrices conventionally contain sudsing agents. Suitable sudsing agents include, but are not limited to, water soluble alkyl sulfates having from 8 to 18 carbon atoms in the alkyl radical, such as sodium lauryl sulfate; water soluble salts of sulfonated monoglycerides of fatty acids having from 10 to 18 carbon atoms in the alkyl radical, such as sodium coconut monoglyceride sulfonate; salts of fatty acid amides of taurines, such as sodium-N-methyl palmitoyl tauride; and salts of fatty acid esters of isethionic acid. Sudsing agents can be used in compositions of this invention in an amount of from about 0.5% to about 5.0% by weight of the total composition.

It is also desirable to include some humectant material in a dentifrice to keep it from hardening. Materials commonly used for this purpose include glycerine, sorbitol, and other polyhydric alcohols. The humectants can comprise up to 35% of the toothpaste composition. Flavoring materials may be included in dentifrice formulations including small amounts of oils of wintergreen and peppermint and sweetening agents such as saccharin, dextrose, levulose and xyletol.

A preferred antiplaque dentifrice preparation is given hereinafter by way of example and is presented for the purpose of illustration but not of limitation.

EXAMPLE I

|  | % By Weight |
|---|---|
| glycerine | 27.00 |
| carboxymethyl cellulose, sodium | 1.50 |
| sodium saccharin | 0.20 |
| sodium benzoate | 0.50 |
| dicalcium phosphate dihydrate | 42.00 |
| dicalcium phosphate anhydrous | 5.00 |
| Arlasolve 200 (polyoxyethylene 20 isohexadecylether) | 0.90 |
| 3,5-dibromo-3'-trifluoromethyl-salicylanilide cetylpyridinium | 0.05 |
| cetylpyridinium chloride | 0.05 |

| | % By Weight |
|---|---|
| deionized water | q.s. to 100.00 |

PROPHYLACTIC PASTE COMPOSITIONS

Compositions of the present invention include, in addition to the described dentifrice preparations, prophylactic paste compositions adapted for relatively infrequent application, e.g., once or twice a year, either professionally, i.e., by a dentist or dental hygienist, or by self-application under professional supervision. Prophylactic paste compositions generally differ from dentifrice compositions in that the cleaning and polishing component thereof is more abrasive (and as a result, is a better tooth cleaner). Since a prophylactic paste composition is applied only once or twice per year, a more abrasive cleaning and polishing agent may safely be employed therein than in a dentifrice preparation, i.e., if the more abrasive cleaning and polishing agent were used in a dentrifice preparation adapted for frequent application, the agent might permanently damage the oral hard tissues.

The compatible substances previously described as suitable cleaning and polishing agents for incorporation in dentifrice preparations may also be employed as the cleaning and polishing component of prophylactic paste compositions. However, in order that the desired optimal level of cleaning and polishing effectiveness be obtained, a different particle size and surface configuration for the substance is needed. For example, a suitable zirconium silicate preparation for use in a dentifrice preparation is disclosed and claimed in U.S. Pat. No. 3,450,813 and suitable zirconium silicate cleaning and polishing agents for use in a prophylactic paste composition is described and claimed in U.S. Pat. Nos. 3,257,282 and 3,330,732.

Other suitable cleaning and polishing agents include mixtures of zirconium silicate and tin dioxide (as set forth and described in U.S. Pat. No. 3,378,445), lava pumice, silica powder, calcium carbonate, and the like.

Prophylactic paste compositions in accordance with the present invention are formulated containing from about 0.05% to 0.2% of the synergistic combinations of antimicrobial agents of the present invention by weight of the total compositions. The cleaning and polishing agent serves as a carrier and is employed with a range of about 20 to 80% by weight depending on the particular formulations as is well known to one skilled in the art.

The prophylactic paste compositions are prepared in a conventional manner and usually include additional ingredients that render the overall composition commercially acceptable. For example, prophylactic paste compositions typically embody conventional components such as bleaching agents, binders, humectants, flavoring agents and the like. A preferred prophylactic paste composition is given hereinafter in Example II, but it should be understood that this example is presented for the purpose of illustration and not of limitation.

| | % By Weight |
|---|---|
| pumice | 55.00 |
| glycerine | 15.00 |
| carboxymethyl cellulose, sodium | 1.50 |
| sodium saccharin | 0.20 |

| | % By Weight |
|---|---|
| cetylpyridinium chloride | 0.025 |
| 3,5-dibromo-3'-trifluoromethyl-salicylanilide | 0.025 |
| flavoring agents | 0.90 |
| water | q.s. to 100.00 |

OTHER COMPOSITIONS

In addition to dentifrice and prophylactic pastes, the present invention may be used in conjunction with other compositions, e.g., topical solutions, mouthwashes and non-abrasive dentifrice gels. The synergistic combinations of the present invention are utilized from about 0.05% to 0.2% by weight of the total compositions. A preferred mouthwash composition is given hereinafter in EXAMPLE III, but is should be understood that this example is presented for the purpose of illustration and not of limitation.

EXAMPLE III

| | % By Weight |
|---|---|
| ethyl alcohol, 95%, USP | 10.0000 |
| 3,5-dibromo-3'-trifluoromethyl-salicylanilide | 0.0500 |
| Pluronic F127 (polyoxyethylene glycol) | 1.7500 |
| glycerine | 5.3000 |
| saccharin, sodium | 0.0500 |
| monosodium glutamate | 0.0496 |
| cetylpyridinium chloride | 0.0500 |
| coloring agents | 0.9000 |
| flavoring agents | 0.2100 |
| deionized water | q.s. to 100% |

A preferred non-abrasive dentifrice gel composition is given hereinafter in EXAMPLE IV, but it should be understood that this example is present for the purpose of illustration and not of limitation.

| | % By Weight |
|---|---|
| Pluronic F-127 (polyoxyethylene glycol) | 26.000 |
| Arlasolve 200 (polyoxyethylene 20 isohexadecylether) | 1.500 |
| cetylpyridinium chloride | 0.025 |
| 3,5-dibromo-3'-trifluoromethyl-salicylanilide | 0.025 |
| potassium sorbate | 0.150 |
| flavoring agents | 0.800 |
| coloring agents | 0.018 |
| water | q.s. to 100% |

In addition to the above carriers, the present invention may be used in conjunction with various other carriers which contact the oral hard and soft tissues during normal use. For example, typically the bristles (either plastic or natural) of a toothbrush, the surfaces of plastic or wooden interdental stimulator, and the surfaces of rubber or plastic dental prophylaxis cup come into close contact with the oral hard tissues, and thus provide a suitable carrier for the active agents of the present invention, with such agents being impregnated in or coated on such carriers.

Similarly, dental flosses and dental tapes utilized to clean the interproximal surfaces of the teeth typically include a waxy, plastic or other material which serves as a carrier for the active agents of the present invention. Typically, such wax may be a water soluble wax, e.g., paraffin, or a water insoluble wax, e.g., polyethylene glycol, polyethylene oxide, polypropylene oxide, methylcellulose and mixtures thereof. Plastics such as vinyl acetate and adhesives such as polyvinyl alcohol are examples of other carriers.

EXAMPLE V

The synergistic antimicrobial efficacy of the combinations of the present invention can be established by the following test procedure. A suitable substrate material, e.g., tooth enamel or a glass slide, is treated with one of the solutions and placed in a human plaque growth media for incubation. The solutions include water alone, 3,5-dibromo-3'-trifluoromethylsalicylanilide alone, cetylpyridinium chloride alone and a combination of 3,5-dibromo-3'-trifluoromethylsalicylanilide and cetylpyridinium chloride. The concentration of the solutions containing a single antimicrobial agent is equal to the concentration of the solution of the combination of antimicrobial agents.

The plaque reduction of each solution is compared to the water solution and a plaque reduction percentage is arrived at by the following equation:

$$\text{plaque reduction percentage} = (1 - \frac{P_A}{P_{WS}}) \times 100$$

wherein $P_A$ is the average weight of the plaque accumulated on the substrates treated with the antimicrobial agent or the combination of antimicrobial agents and $P_{WS}$ is the average weight of the plaque accumulated on the substrates treated with the water solution.

The plaque reduction percentages for each solution containing a single antimicrobial are averaged and then compared to the plaque reduction percentage of the combination of antimicrobials. The results of six runs are shown in Table I as follows:

Table I

| Run | Average of Plaque Reduction Percentages of Solutions Containing a Single Antimicrobial Agent | Plaque Reduction Percentage of Solution of Combination of Antimicrobial Agents | % Increase of Plaque Reduction |
|---|---|---|---|
| 1 | 63% | 79% | 25% |
| 2 | 70 | 66 | −5 (derease) |
| 3 | 47 | 68 | 40 |
| 4 | 69 | 77 | 12 |
| 5 | 69 | 90 | 23 |
| 6 | 70 | 91 | 30 |

As can be seen from the above results, the combinations of antimicrobial agents exhibit a synergistic increase in plaque reduction over the individual antimicrobials at the same concentration levels. Run 2 did not exhibit this increase but can be explained by the adverse microbial growth conditions periodically observed in this type of in vitro assay.

EXAMPLE VI

The non-staining properties of the synergistic antimicrobial combinations of the present invention are demonstrated by the following modified Nordbö staining procedure.

This procedure is set forth in an article by H. Nordbö, Discoloration of Human Teeth by a Combination of Chlorhexidine and Aldehydes or Ketones In Vitro, Scand. J. Dent. Res. 79:356–361 (1971). This procedure involves the Maillard or Browning Reaction whereby a salivary protein, such as mucin, reacts with the active aldehyde group of carbohydrates, such as acetaldehyde, fructose and the like, to produce a furfural-type or pigmented compound that tenaciously adheres to an artificial enamel surface.

Three solutions were prepared each containing 0.4% mucin and 4% acetaldehyde in a 0.1 M potassium phosphate buffer solution, pH 7, and a final volume of 10 milliliters. To one solution 2% chorhexidine (a known staining agent) is added and to a second solution was added 0.25% of a mixture of cetylpydinium chloride/3,5-dibromo-3'-trifluoromethylsalicylanilide in a 1:1 ratio. Hydroxyapatite discs were added into each 10 milliliter solution and incubated at a temperature of 37° C. for three days and then removed. Said discs were visually examined and analytical measurements taken to quantitate staining. The disc from the solution containing the chlorhexidine exhibited excessive staining whereas the disc from the solution containing the cetylpyridinium chloride/3,5-dibromo-3'-trifluoromethylsalicylanilide mixture demonstrated significantly reduced staining and compared favorably with the third solution which did not contain either the chlorhexidine staining agent or the antimicrobial mixtures of the present invention.

What is claimed is:

1. An oral antimicrobial composition comprising as the active antimicrobial ingredients a synergistic combination of 3,5-dibromo-3'-trifluoromethylsalicylanilide and cetylpyridinium chloride wherein the 3,5-dibromo-3'-trifluoromethylsalicylanilide and cetylpyridinium chloride are present in a ratio of from about 10:1 to about 1:10.

2. The oral antimicrobial composition of claim 1 wherein the 3,5-dibromo-3'-trifluoromethylsalicylanilide and cetylpyridinium chloride are present in an amount of from about 0.05 to about 0.20% by weight of the total composition.

3. The oral antimicrobial composition of claim 1 wherein the 3,5-dibromo-3'-trifluoromethylsalicylanilide and cetylpyridinium chloride are present in a ratio of about 1:1.

4. A method of inhibiting the formation of dental plaque on the teeth comprising the application thereon of an oral antimicrobial composition comprising as the active antimicrobial ingredients from about 0.05 to about 0.20% by weight of the composition of a synergistic combination of 3,5-dibromo-3'-trifluoromethylsalicylanilide and cetylpyridinium chloride wherein the 3,5-dibromo-3'-trifluoromethylsalicylanilide and cetylpyridinium chloride are present in a ratio of from about 10:1 to about 1:10.

5. The method of claim 4 wherein the 3,5-dibromo-3'-trifluoromethylsalicylanilide and cetylpyridinium chloride are present in a ratio of about 1:1.